US008498750B2

(12) United States Patent
Stevens et al.

(10) Patent No.: US 8,498,750 B2
(45) Date of Patent: Jul. 30, 2013

(54) SYSTEM FOR MONITORING A TRANSIENT FLUID

(75) Inventors: Jed Stevens, Colorado Springs, CO (US); Mike Uffer, Lake Forest, CA (US); Martin W. Pickett, San Juan Capistrano, CA (US); Vicky B. Roberts, Mission Viejo, CA (US)

(73) Assignees: Velcon Filters, LLC, Colorado Springs, CO (US); Cla-Val, Costa Mesa, CA (US)

( * ) Notice: Subject to any disclaimer, the term of this patent is extended or adjusted under 35 U.S.C. 154(b) by 693 days.

(21) Appl. No.: 12/644,084

(22) Filed: Dec. 22, 2009

(65) Prior Publication Data

US 2010/0161139 A1 Jun. 24, 2010

Related U.S. Application Data

(60) Provisional application No. 61/140,098, filed on Dec. 23, 2008.

(51) Int. Cl.
*G05D 7/00* (2006.01)
(52) U.S. Cl.
USPC ........... 700/282; 700/271; 73/61.43; 340/603
(58) Field of Classification Search
USPC ... 700/271, 282; 340/603, 606, 609; 73/61.43
See application file for complete search history.

(56) References Cited

U.S. PATENT DOCUMENTS

| 4,403,584 | A | * | 9/1983 | Suzuki et al. ............ 123/406.23 |
| 4,901,751 | A | * | 2/1990 | Story et al. .................... 137/312 |
| 5,722,469 | A | | 3/1998 | Tuminaro |
| 5,779,911 | A | * | 7/1998 | Haug et al. .................... 210/739 |
| 6,710,878 | B1 | | 3/2004 | Dean et al. |
| 2002/0023505 | A1 | * | 2/2002 | Jackson et al. ............. 73/864.73 |
| 2006/0174941 | A1 | * | 8/2006 | Cohen et al. .................... 137/93 |
| 2008/0000839 | A1 | * | 1/2008 | Drewelow ..................... 210/739 |
| 2009/0078038 | A1 | * | 3/2009 | Ushigusa et al. ................ 73/195 |
| 2009/0123340 | A1 | * | 5/2009 | Knudsen et al. .............. 422/105 |
| 2009/0306830 | A1 | * | 12/2009 | Cummings et al. ........... 700/282 |

FOREIGN PATENT DOCUMENTS

| DE | 206 439 | 1/1984 |
| GB | 2 451 939 | 2/2009 |

OTHER PUBLICATIONS

Cla-Val, Service Training Manual & Trouble Shooting Guide "Simple Solutions Plus Leaning with a Purpose", 2003, CLA-VAL, p. 1-190.*

* cited by examiner

*Primary Examiner* — Sean Shechtman
(74) *Attorney, Agent, or Firm* — Fraser Clemens Martin & Miller LLC; J. Douglas Miller

(57) ABSTRACT

A system for monitoring a transient flow of a fluid for the presence of contaminants is disclosed. The system includes a fluid control valve having a body defining a fluid flow path therethrough. A fluid monitoring device is in fluid communication with the fluid flowing through the control valve. The fluid monitoring device is adapted to monitor the fluid flowing through the control valve for contaminants.

20 Claims, 2 Drawing Sheets

SYSTEM FOR MONITORING A TRANSIENT FLUID

CROSS-REFERENCE TO RELATED APPLICATION

This application claims the benefit of U.S. provisional patent application Ser. No. 61/140,098 filed Dec. 23, 2008, hereby incorporated herein by reference in its entirety.

FIELD OF THE INVENTION

The present invention relates to a system for monitoring the quality of a transient fluid, and more particularly to a fluid control valve including a fluid monitor to detect the presence of contaminants in the transient fluid.

BACKGROUND OF THE INVENTION

It is necessary to monitor fuel such as aviation fuel, diesel fuel, or other fuels for vehicles and combustion devices such as heaters and boilers, for example, to determine whether the fuel includes contaminants. As sources and types of fuel have increased, the need to monitor the quality of the fuel to militate against contaminants being introduced into an engine, a heater, or a boiler, for example, has increased.

In many applications, individual fuel samples are taken periodically from a source of fuel and tested to determine whether any contaminants are contained therein. Taking periodic samples is typically time consuming and provides no test data in respect of the quality of the fuel supplied between samples.

Real time monitoring of the quality of transient fuel is a growing practice for suppliers of fuel. Typically, a real time fuel monitoring device can be readily included in a newly designed fuel supply system. However, it has been found that retrofitting an existing fuel supply system with a real time fuel monitoring device can be difficult due to space limitations and other constraints typically encountered with the existing fuel supply systems.

It would be desirable to produce a system for monitoring the quality of a transient fluid adapted to be utilized with an existing fluid supply system, wherein an ease of installation of the system is maximized.

SUMMARY OF THE INVENTION

Concordant and consistent with the present invention, a system for monitoring the quality of a transient fluid adapted to be utilized with an existing fluid supply system, wherein an ease of installation of the system is maximized, has surprisingly been discovered.

The above objective, as well as others, may be achieved by a system for contamination analysis of a transient fluid comprising: a fluid control valve having a housing defining a fluid flow path therethrough; and a fluid monitoring device in fluid communication with the fluid flowing through the control valve to detect contaminants in the fluid, wherein the flow of fluid through the control valve is substantially stopped upon a detection of a selected predetermined level of contaminants.

In another embodiment, a system for contamination analysis of a transient fluid comprises: a fluid control valve having a body defining a fluid flow path therethrough, wherein the body includes an aperture formed therein; and a fluid monitoring device in fluid communication with the fluid flowing through the control valve to detect contaminants in the fluid, at least a portion of the fluid monitoring device disposed in the aperture, wherein a flow rate of fluid through the control valve is controlled based upon a detection of a predetermined level of contaminants.

In yet another embodiment, a system for contamination analysis of a transient fluid comprises: a fluid control valve having a body defining a fluid flow path therethrough, wherein the body includes an aperture formed therein and at least one wall adjacent the aperture and protruding outwardly from the body; and a fluid monitoring device in fluid communication with the fluid flowing through the control valve to detect contaminants in the fluid, at least a portion of the fluid monitoring device disposed in the aperture, wherein a flow rate of fluid through the control valve is controlled based upon a detection of a predetermined level of contaminants.

BRIEF DESCRIPTION OF THE DRAWINGS

The above, as well as other objects and advantages of the invention, will become readily apparent to those skilled in the art from reading the following description of an embodiment of the invention when considered in the light of the accompanying drawings, in which.

DETAILED DESCRIPTION OF THE PREFERRED EMBODIMENT OF THE INVENTION

The following detailed description and appended drawings describe and illustrate various exemplary embodiments of the invention. The description and drawings serve to enable one skilled in the art to make and use the invention, and are not intended to limit the scope of the invention in any manner.

Figure 1:
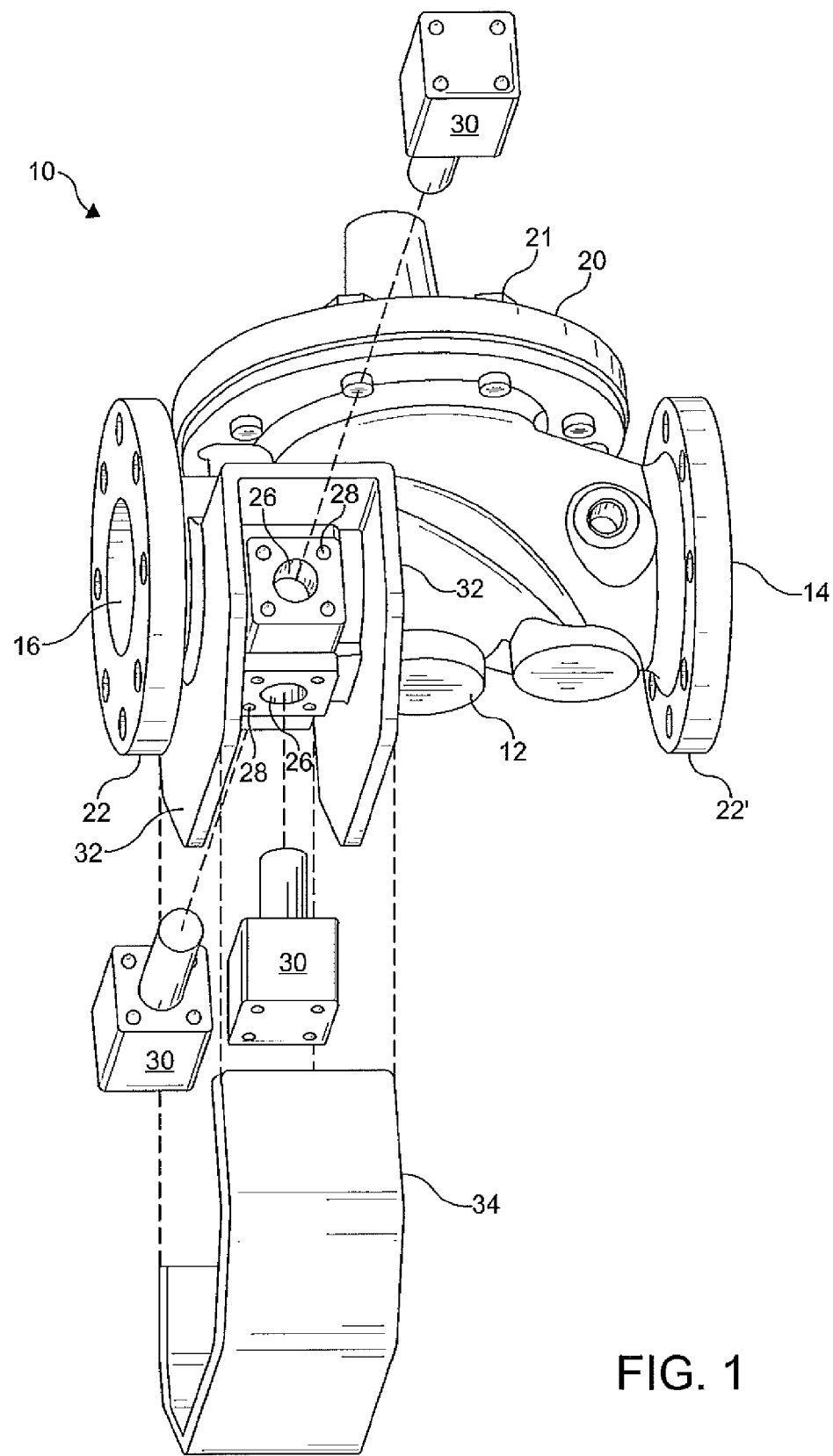
FIG. 1 is a perspective view of a fluid control valve of a system for monitoring the quality of a transient fluid according to an embodiment of the present invention.
Figure 2:
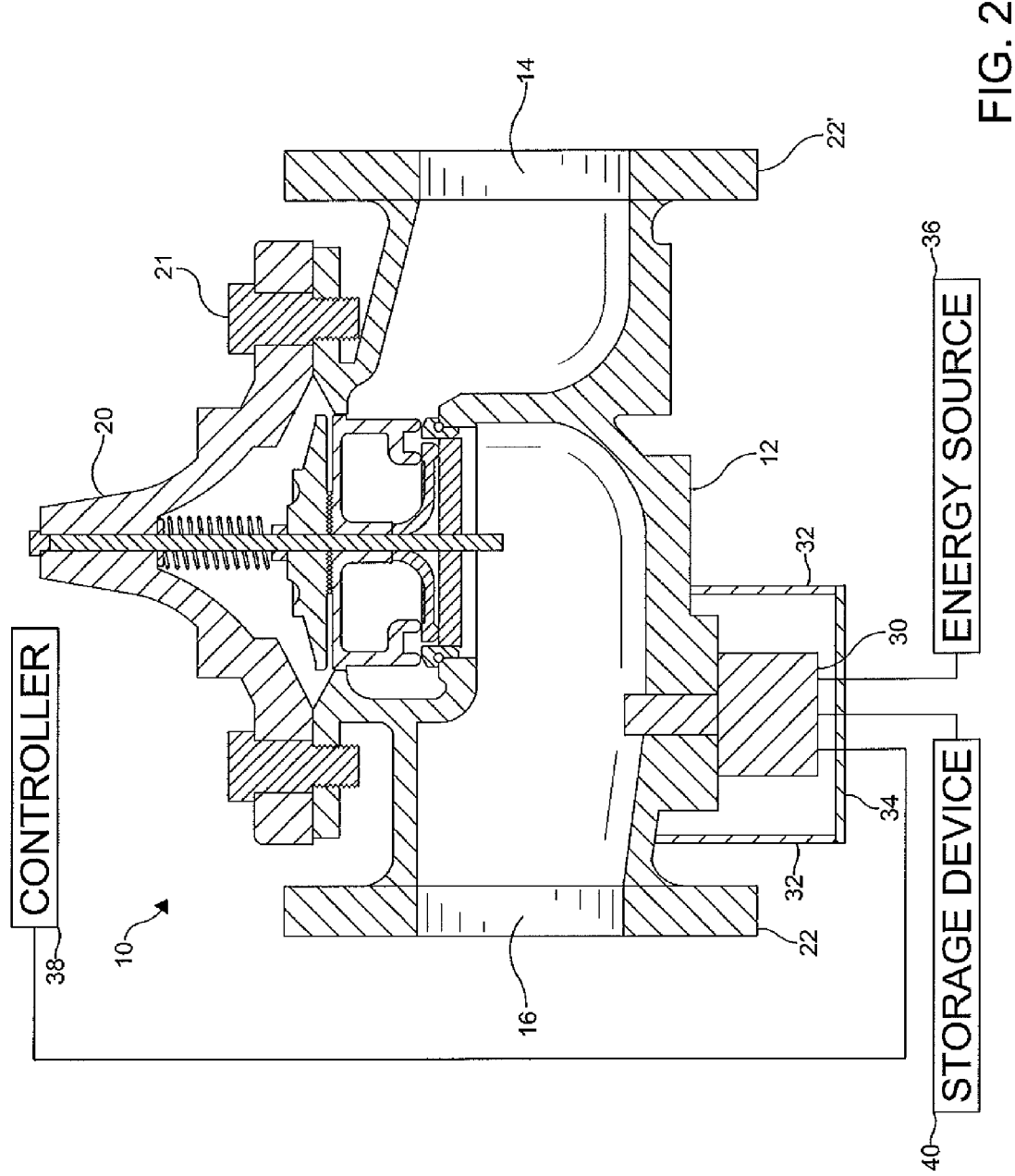
FIG. 2 is a cross-sectional view of the fluid control valve of FIG. 1 including a schematic representation of components of the system for monitoring the quality of a transient fluid.

FIGS. 1-2 illustrate a system for monitoring the quality of a transient fluid. In the illustrated embodiment, the fluid being monitored is a fuel such as aviation fuel or diesel fuel, for example. It should be understood that the system can be employed to monitor the quality of other types of fuels and other fluids, as desired.

The system includes a fluid control valve 10 having a body 12 with a fluid inlet 14 and a fluid outlet 16 defining a flow path therethrough, and an opening into an interior of the body 12. As a non-limiting example, the control valve 10 is similar to a 100-01 valve assembly manufactured by the CLA-VAL Company. However, other valve assemblies can be used. A cover 20 for the opening is removably attached to the body 12 to form a substantially fluid tight seal therebetween. In the illustrated embodiment, a mechanical fastener 21 is employed together with sealing means (not shown) to facilitate forming the substantially fluid tight seal. However, it should be understood that other means can be employed to form the substantially fluid tight seal between the body 12 and the cover 20, as desired. A pair of flanges 22, 22' is formed on the body 12 circumscribing the fluid inlet 14 and the fluid outlet 16. The flanges 22, 22' facilitate joining the valve 10 to associated fluid conduits as shown in FIG. 2. It should be understood that other means to join the valve 10 to the associated fluid conduits may be formed on the body 12 such as a male or a female threaded end, for example. Additionally, it should be understood that the valve 10 can be joined to the associated conduits employing other means such as welding, for example. It should be understood that the valve 10 typically includes means disposed therein to facilitate the regulation of a flow of the fluid therethrough. Additionally, it should be understood that the valve 10 can be manufactured to a custom size or any standard size. When manufactured to conform to a standard size valve, the valve 10 can be readily employed to replace a valve in an existing fluid supply system.

The body 12 includes at least one aperture 26 formed therein. Means to attach 28 a fluid monitoring device 30 to the body 12 is formed in the body 12 adjacent the aperture 26. The means to attach 28 is adapted to form a substantially fluid tight seal between the fluid monitoring device 30 and the body 12. The aperture 26 provides fluid communication between the interior of the body 12 and the fluid monitoring device 30.

In certain embodiments, the body 12 includes an outwardly protruding wall 32 disposed adjacent the aperture 26. A cover plate 34 is removably coupled to the wall 32 to at least partially enclose the aperture 26 and the fluid monitoring device 30 therein. Any means for coupling the cover plate 34 and the wall 32 can be used to form a substantially fluid tight seal therebetween. It is understood that any number of walls 32 can be used. It is further understood that the cover plate 34 may have any size and shape as desired.

In the illustrated embodiment, three apertures 26 are formed in the body 12 of the valve 10 with the means to attach 28 formed adjacent thereto. The three apertures 26 allow three separate components of the fluid monitoring device 30 to be attached to the body 12 in fluid communication with the interior of the body 12. Favorable results have been obtained employing a fluid monitoring device such as the contaminant analyzer disclosed in U.S. patent application Ser. No. 11/627, 105, now U.S. Pat. No. 7,518,719, hereby incorporated herein by reference in its entirety. However, it should be understood that other fluid monitoring devices can be used as desired. Additionally, it should be understood that components of the fluid monitoring device 30 can be disposed within the interior of the body 12 such as a flow sensor and a calibration standard, for example. It is further understood that the fluid monitoring device 30 can have any shape and size and include any number of components, as desired.

The fluid monitoring device 30 is in communication with a source of electrical energy 36. The flow sensor can be employed to selectively provide electrical communication between the source of electrical energy 36 and the fluid monitoring device 30, wherein electrical energy is supplied to the fluid monitoring device 30 upon a detection of fluid flow through the valve 10, and electrical energy to the fluid monitoring device 30 is interrupted upon a detection of a cessation of fluid flow through the valve 10.

In certain embodiments, the source of electrical energy 36 is a flow powered turbine-style electrical generator disposed within the valve 10. The generator is adapted to produce electrical energy upon a flow of the fluid through the valve 10. The generator is in electrical communication with the fluid monitoring device 30 and employed to power the fluid monitoring device 30. The use of the generator to provide electrical energy to the fluid monitoring device 30 eliminates a need to provide an external source of power for the fluid monitoring device 30. Additionally, the generator can provide an automatic initiation and cessation of fluid monitoring upon the flow of the fluid or the stoppage of the flow of fluid, respectively.

It should be understood that the valve 10 and the fluid monitoring device 30 can be adapted to cause the valve 10 to close, or otherwise adjust a flow of the fluid therethrough, upon a detection of a selected predetermined level of contaminants in the fluid by the fluid monitoring device 30. In certain embodiments, a controller 38 is in signal communication with the fluid monitoring device 30 to receive a control signal therefrom and selectively control a flow of fluid through the valve 10 based on the control signal. As a non-limiting example, the controller 38 is a solenoid valve adapted to actuate the control valve 10 to vary a flow rate of the fluid through the control valve 10. It is understood that the solenoid may be energized to cause the control valve 10 to open or close, as desired. However, other controllers, actuators, or other devices, internal or external to the valve 10 can be adapted to stop or otherwise modify the flow of the fluid through the valve 10 upon a detection of a selected predetermined level of contaminants, for example. It is further understood that the controller 38 can be in communication with an energy source such as the electrical energy source 36, for example, to facilitate an operation thereof.

Further, the fluid monitoring device 30 can provide a warning signal such as an audible or a visual signal, for example, upon a detection of a selected predetermined level of a contaminant in the fluid. Additionally, the fluid monitoring device 30 can be in communication with an electronic storage device 40 adapted to receive and retain data from the fluid monitoring device 30. The storage device 40 may be a single storage device or may be multiple storage devices. Furthermore, the storage device 40 may be a solid state storage system, a magnetic storage system, an optical storage system or any other suitable storage system or device. Any data can be stored in the storage device 40 such as the parameters measured and calculated by the fluid monitoring device 30, for example. It is further understood that certain known parameters may be stored in the storage device 40 to be retrieved by the fluid monitoring device 30. The data can be accessed as desired for analysis by a person or an algorithm, for example.

In use, the valve 10 is installed in a fluid supply conduit (e.g. joined to the associated fluid conduits wherein the fluid flowing therein enters the interior of the body 12 of the valve 10 through the fluid inlet 14; flows past the fluid monitoring device 30 attached to the body 12; and exits the valve 10 through the fluid outlet 16. The flow of the fluid through the valve 10 is detected by the flow sensor causing electrical communication between the fluid monitoring device 30 and the source of electrical energy 36, which is employed to energize the fluid monitoring device 30. The flow of the fluid and subsequent energizing of the fluid monitoring device 30 initiates the monitoring of the fluid. Electrical energy continues to be supplied to the fluid monitoring device 30 while fluid continues to flow through the valve 10, which provides substantially continuous fluid monitoring while fluid is flowing through the valve 10. When the fluid stops flowing through the valve 10, the flow sensor interrupts the supply of electrical energy to the fluid monitoring device 30 and monitoring of the fluid is stopped. It should be understood that the flow of the fluid can be stopped by an automated or manual actuation of the valve 10 or another valve of the fluid supply system; or by other means such as deactivating a fluid pump of the fluid supply system, for example.

The fluid monitoring device 30 substantially continuously monitors the fluid flowing therethrough for contaminants. Further, the fluid monitoring device 30 can be adapted to provide and/or trigger a signal such as an audible or visual signal, upon a detection of a selected predetermined level of contaminants. It should be understood that the audible or the visual signal can be powered by an energy source such as the electrical energy source 36, for example. Additionally, it should be understood that the electrical energy source 36 to power the controller 38 or the signal can be a public electrical grid, a generator disposed in the valve, or an electrical storage battery charged by the generator, for example.

The fluid monitoring device 30 can also be in communication with the storage device 40 to record data from the fluid monitoring device 30. The data can be recorded in any usable format now know or later developed to facilitate a review and analysis of the detected contaminant levels. Typically, the storage device 40 is powered with electrical energy from an external source such as a public electrical grid, for example. However, the storage device 40 can also be powered by electrical energy from the generator, or an electrical storage battery charged by the generator, for example.

Additionally, it should be understood that the valve 10 can be manufactured to a custom size or any standard size. When manufactured to conform to a standard size valve, the valve 10 can be readily employed to replace a valve in an existing fluid supply system.

The body 12 of the valve 10 for the system for monitoring the quality of the transient fluid is typically formed to allow the valve 10 to replace an existing valve in the fluid supply system. The fluid monitoring device 30 is incorporated into the body 12 of the valve 12 to minimize the physical size of the valve 10. Accordingly, the system for monitoring the quality of the transient fluid facilitates retrofitting an existing fluid supply system to have substantially continuous fluid monitoring capability by replacing an existing valve with the valve 10 including the fluid monitoring device 30.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. A system for contamination analysis of a transient fluid comprising:
   a fluid control valve including:
      a body including an inlet, an outlet, a fluid flow path passing through an interior of the body from the inlet to the outlet, and a first aperture providing access to the fluid flow path; and
      a fluid monitoring device configured to detect contaminants in the fluid flow path coupled to the body, wherein the first aperture provides fluid communication between the interior of the body and the fluid monitoring device;
      wherein the fluid control valve is configured to control a flow rate of the transient fluid through the fluid flow path; and
   a controller in communication with the fluid monitoring device to receive a control signal therefrom and selectively control the flow rate of the transient fluid through the fluid flow path with the fluid control valve based upon detection of a predetermined level of contaminants in the fluid flow path.

2. The system of claim 1, wherein the fluid monitoring device further comprises a flow sensor disposed within the body.

3. The system of claim 1, wherein the fluid monitoring device further comprises a calibration standard disposed within the body.

4. The system of claim 1, further comprising a source of electrical energy in communication with the fluid monitoring device.

5. The system of claim 4, wherein the fluid monitoring device further comprises a flow sensor disposed within the body to selectively provide electrical communication between the source of electrical energy and the fluid monitoring device, wherein electrical energy is supplied to the fluid monitoring device upon a detection of a flow of the transient fluid through the fluid flow path and electrical energy to the fluid monitoring device is interrupted upon cessation of the flow of the transient fluid through the fluid flow path.

6. The system of claim 4, wherein the source of electrical energy comprises a flow powered turbine-style electrical generator disposed within the fluid control valve, wherein the generator is configured to produce electrical energy upon a flow of the transient fluid through the fluid control valve.

7. The system of claim 1, further comprising a storage device in communication with the fluid monitoring device, wherein the storage device is configured to receive and retain data from the fluid monitoring device.

8. A fluid control valve for monitoring a transient fluid comprising:
   a body including an inlet, an outlet, a fluid flow path passing through an interior of the body from the inlet to the outlet, and a first aperture providing access to the fluid flow path; and
   a fluid monitoring device configured to detect contaminants in the fluid flow path coupled to the body, wherein the first aperture provides fluid communication between the interior of the body and the fluid monitoring device;
   wherein the fluid control valve is configured to control a flow rate of the transient fluid through the fluid flow path based upon detection of a predetermined level of contaminants in the fluid flow path.

9. The fluid control valve of claim 8, wherein the body further comprises a second aperture providing fluid communication between the interior of the body and the fluid monitoring device.

10. The fluid control valve of claim 9, wherein the fluid monitoring device further comprises a flow sensor or a calibration standard disposed within the body through the second aperture.

11. The fluid control valve of claim 9, wherein the body further comprises a third aperture providing fluid communication between the interior of the body and the fluid monitoring device.

12. The fluid control valve of claim 11, wherein the fluid monitoring device further comprises a flow sensor disposed within the body through one of the first and second apertures and a calibration standard disposed within the body through the other of the first and the second apertures.

13. The fluid control valve of claim 8, wherein the fluid monitoring device comprises a flow sensor.

14. The fluid control valve of claim 13, wherein the fluid monitoring device is configured to detect contaminants in the fluid flow path when the flow sensor detects a flow of the transient fluid through the fluid flow path.

15. The fluid control valve of claim 8, wherein the body further comprises a wall partially enclosing the first aperture and the fluid monitoring device.

16. The fluid control valve of claim 15, further comprising a cover removably coupled to the wall to at least partially enclose the first aperture and the fluid monitoring device.

17. The fluid control valve of claim 8, wherein the fluid control valve is further configured to provide an audible signal or a visual signal upon detection of a selected predetermined level of contaminants in the fluid flow path.

18. A method of controlling a flow of a transient fluid comprising:
   providing a flow of a transient fluid through a fluid control valve, the fluid control valve comprising: a body including an inlet, an outlet, a fluid flow path passing through an interior of the body from the inlet to the outlet, and a first aperture providing access to the fluid flow path; and a fluid monitoring device configured to detect contaminants in the fluid flow path coupled to the body, wherein the first aperture provides fluid communication between the interior of the body and the fluid monitoring device; wherein the fluid control valve is configured to control a flow rate of the transient fluid through the fluid flow path based upon detection of a predetermined level of contaminants in the fluid flow path;

detecting whether a predetermined level of contaminants are in the fluid flow path using the fluid monitoring device; and adjusting the flow of the transient fluid using the fluid control valve upon detecting the predetermined level of contaminants in the fluid flow path.

19. The method of claim 18, further comprising providing an audible signal or a visual signal upon detection of a selected predetermined level of contaminants in the fluid flow path.

20. The method of claim 18, wherein the fluid monitoring device further comprises a flow sensor and the method further comprises detecting the flow of transient fluid through the fluid control valve using the flow sensor and causing electrical communication between the fluid monitoring device and a source of electrical energy to energize the fluid monitoring device.

* * * * *